(12) United States Patent
Nijenbanning et al.

(10) Patent No.: US 6,979,304 B2
(45) Date of Patent: Dec. 27, 2005

(54) GRAVITY OPERATED LOCKING HINGE

(75) Inventors: Gert Nijenbanning, Oldenzaal (NL);
Josephus Anton Goudsmit, Almere Stad (NL)

(73) Assignee: Bandage -en Corsetindustrie Basko B.V., Amsterdam (NL)

(*) Notice: Subject to any disclaimer, the term of this patent is extended or adjusted under 35 U.S.C. 154(b) by 73 days.

(21) Appl. No.: 10/239,241

(22) PCT Filed: Mar. 22, 2001

(86) PCT No.: PCT/NL01/00236

§ 371 (c)(1),
(2), (4) Date: Feb. 20, 2003

(87) PCT Pub. No.: WO01/70149

PCT Pub. Date: Sep. 27, 2001

(65) Prior Publication Data

US 2003/0153854 A1  Aug. 14, 2003

(30) Foreign Application Priority Data

Mar. 23, 2000 (NL) .................................. 1014732

(51) Int. Cl.[7] .............................................. A61F 5/00
(52) U.S. Cl. ............................. 602/16; 602/12; 602/23; 602/26
(58) Field of Search ............................. 602/5, 12, 16, 602/23, 26, 60, 62; 16/317, 292

(56) References Cited

U.S. PATENT DOCUMENTS

| 2,591,373 | A | * | 4/1952 | Petruch | 602/26 |
| 2,646,793 | A | * | 7/1953 | Swiech et al. | 602/16 |
| 3,826,251 | A | | 7/1974 | Ross | |
| 4,252,111 | A | * | 2/1981 | Fletcher et al. | 602/16 |
| 5,188,584 | A | * | 2/1993 | Petrofsky et al. | 602/16 |
| 5,315,722 | A | | 5/1994 | Djie | |
| 5,369,843 | A | | 12/1994 | Yu | |
| 5,399,154 | A | | 3/1995 | Kipnis et al. | |
| 5,425,700 | A | | 6/1995 | Aaserude et al. | |
| 6,004,283 | A | * | 12/1999 | Young | 602/16 |
| 6,500,138 | B1 | * | 12/2002 | Irby et al. | 602/26 |
| 6,746,414 | B1 | * | 6/2004 | Devreese | 602/26 |
| 2004/0225442 | A1 | * | 11/2004 | Lidolt et al. | 602/16 |

FOREIGN PATENT DOCUMENTS

DE  197 47 020   4/1999
EP  0 872 224    10/1998

* cited by examiner

Primary Examiner—Henry Bennett
Assistant Examiner—Amanda Wieker
(74) Attorney, Agent, or Firm—Young & Thompson (57) ABSTRACT

A hinge provided with a first part and a second part, which parts are able to turn relative to one another from a first position of the hinge into a second position of the hinge, the hinge being provided with a locking element for locking the hinge in the first position thereof, which locking element can move between a first position for releasing the hinge and a second position for locking the hinge. A locking element is fitted in a movable manner for moving under the influence of gravity, between the first position and the second position when the hinge sways.

23 Claims, 13 Drawing Sheets

GRAVITY OPERATED LOCKING HINGE

BACKGROUND OF THE INVENTION

The invention relates to a hinge provided with a first part and a second part, which parts are able to turn relative to one another from a first position of the hinge into a second position of the hinge, the hinge being provided with a locking element for locking the hinge in the first position thereof, which locking element can move between a first position for releasing the hinge and a second position for locking the hinge.

The hinge according to the present invention is in particular suitable as an orthopedic knee joint. Orthopedic knee joints are, for example, used by patients who are not capable of stabilising the knee joint without aids. Without aids, the knees of such patients would give way when they walk. When walking, the leg moves from the point in time that the heel makes contact with the ground from a position in which it is stretched forward into the so-called mid-position stage in which the leg is essentially perpendicular under the body. Because the body is moving forward relative to the leg, the leg will then be pointing somewhat backwards with respect to the body. The leg then returns via the so-called swinging stage back to the initial position in which the heel makes contact with the ground.

For paralysis patients, for example, in order to be able to walk safely it is necessary that an orthopedic knee joint stabilises the patient's knee at the end of the standing stage, but in any event from the point in time when the heel of the foot comes into contact with the ground to at least the mid-position stage. The simplest solution for achieving this is to make use of an orthesis that fixes the thigh relative to the lower leg when walking. This can be effected, for example, by means of a hinge that is locked while walking. At the point in time when a user sits down, the user can unlock the hinge in order to make it possible to bend the leg. A significant disadvantage of a hinge of such simple construction is that the user has to walk with a stiff leg. The ease of use of orthopedic knee joints is appreciably improved if the orthopedic knee joint is automatically unlocked when the swinging stage starts. With automatic unlocking of the hinge, a user is able to walk in a normal manner. At the point in time when the leg is placed on the ground, the knee is stabilised with the aid of the orthopedic knee joint, so that the user can bear safely on the locked knee. The hinge is unlocked at the point in time when the swinging stage has to start. This can take place safely because the weight of the user has then been transferred to the other leg.

Orthopedic knee joints with which the joint can be unlocked at the start of the swinging stage are known in the state of the art. U.S. Pat. Nos. 5,490,831 and 2,943,622 and European Patent Application EP 0 872 224 disclose knee joints with which the presence of stress on a user's heel is used as a signal for locking the knee joint. According to these publications a detection element is present in the heel, which detection element is, for example, connected by a cable or rod to a locking element. As long as the detection element detects that stress is being exerted on the heel, the joint is locked by means of the locking element. However, as soon as there is no longer any stress on the heel, the knee joint is released. A significant disadvantage of the solution according to the said documents is that the knee joint will also be unlocked if stress is exerted on, for example, the front of the user's foot. If the user is negotiating an obstacle, such as, for example, a kerb, with his/her leg, the detection element will not detect any stress on the heel and will release the hinged joint. The user's knee joint will consequently give way. As a result of this limitation, the solution according to the abovementioned documents is impractical and, moreover, dangerous. An alternative solution for providing automatic unlocking of the joint is disclosed in U.S. Pat. No. 3,826,251. According to this US Patent the presence of an axial force on the hinge is used to either lock or release the hinge. A significant disadvantage of this solution is that the bulk of the reactive force from the ground is absorbed by the leg. That is to say this reactive force is not absorbed by the hinge and can also be not be detected by the hinge. This means that these hinges do not work well in practice.

U.S. Pat. No. 4,632,096 discloses a hinge that can be released by turning the foot relative to the leg. A cable is attached to the foot, which cable is connected to a locking element in the knee joint. By turning the foot, locking of the hinge can be released with the aid of the cable.

The disadvantage of the solution according to this US Patent is that unlocking can take place only by active turning of the foot. This means that the user must be prepared to turn his/her foot at every step. Furthermore, in this solution a coupling is always needed between the knee joint and the foot or the ankle joint. This makes the system susceptible to malfunctions and in the majority of cases the aid in which the knee joint is incorporated will have to be equipped with a foot section. Moreover, here again the functioning of the system is dependent on the ground surface.

SUMMARY OF THE INVENTION

In view of the abovementioned disadvantages of the solutions according to the prior art, the aim of the present invention is to provide a hinge of the abovementioned type, and in particular an orthopedic knee joint that is provided with a hinge of the type mentioned in the preamble, wherein the hinge is provided with a construction such that locking and release of the hinge takes place automatically while walking, without the user actively having to deactivate the locking.

Said aim is achieved according to the present invention in that a locking element is fitted in a movable manner for moving under the influence of gravity between the first position and the second position when the hinge sways.

If the hinge according to the present invention is used as an orthopedic knee joint, the hinge as a whole will sway with respect to the vertical during use. During swaying of the hinge, the locking element will be moved under the influence of gravity between, respectively, the first position for releasing the hinge and the second position for locking the hinge.

When the hinge is used in an orthopedic knee joint, the hinge is moved into the first position in the swinging stage. In order for the hinge to function well, it is necessary that the hinge is then locked with the aid of the locking element. This means that the locking element must have been brought into the second position at least by the end of the swinging stage. The user will then exert stress on the leg, and thus on the hinge. Because the hinge is locked with the aid of the locking element, the user is able to walk safely. Because the hinge will sway with respect to the vertical during the walking movement, it is possible for the locking element to be moved into the first position under the influence of gravity, in order to release the hinge, just before a new swinging stage starts. This movement of the locking element into the first position thereof takes place under the influence of gravity and thus occurs automatically. The user does not have to take any further measures in order to move the locking element. Because the locking element is in the first position, the locking element will release the hinge and it is possible to move the first part of the hinge relative to the second part. That is to say, the user's thigh is able to pivot with respect to the lower leg. As a result a user is able to bend his/her knee in a normal manner and to walk in a normal manner. As a result of the swinging stage, the hinge returns to the first position thereof, the hinge again being locked in the first position with the aid of the locking element.

For the sake of clarity it is pointed out that in the present invention specific reference is made to the use of the hinge according to the invention in an orthopedic knee joint. It is clear that the hinge according to the present invention is also suitable for other joints, such as, for example, an orthopedic elbow joint, an ankle joint or a hip joint. The present invention is therefore explicitly not restricted to orthopedic knee joints.

According to the invention it is advantageous that when the hinge is in the first position the second part is essentially in the extension of the first part, the second part being at an angle with respect to the first part when the hinge is in the second position.

In order to be able to use the hinge according to the invention as an orthopedic knee joint it is necessary to connect elements for coupling the knee joint to the user's leg or leg prosthesis to the first part and the second part of the joint. In use, it is advantageous that the first part and the second part are essentially in line in the first position of the hinge with this arrangement.

According to the invention it is advantageous that the locking element is fixed in the hinge in such a way that it is able to turn or slide, the locking element being able to move or pivot about the axis of rotation thereof under the influence of gravity.

The locking element can be fitted in the hinge in various ways. By fixing the locking element such that it can turn, the position of the locking element is unambiguously defined at all times. Furthermore, the construction is relatively simple.

What is achieved as a result of this measure is that the locking element has two stable end positions. Depending on the position of the hinge, the locking element will be moved into either the first position thereof or the second position thereof.

According to the invention, it is furthermore advantageous that the center of gravity of the locking element is some distance away from the axis of rotation of the locking element.

It is furthermore advantageous that the center of gravity of the locking element is located above the axis of rotation of the locking element when the hinge is in the use position.

In order to increase the force with which the locking element locks the joint it is furthermore possible that the second part is provided with a projection, which projection describes a path when the second part pivots relative to the first part, the locking element allowing the projection a free movement path when it is in the first position thereof and being present in the movement path of the projection when it is in the second position thereof.

It is pointed out that mechanical reversal, that is to say the projection is fixed to the first part instead of to the second part, is also possible. What is achieved by making use of a projection that describes a path and moving the locking element respectively into or out of the path is that the locking element can be arranged some distance away from the axis of rotation of the first part of the hinge relative to the second part of the hinge.

According to the invention it is furthermore advantageous that the hinge is provided with a first and a second stop in order to limit the movement of the locking element in, respectively, the first and the second position thereof.

The presence of these stops ensures that the maximum stroke of the locking element from, respectively, the first position into the second position thereof is restricted, so that what is achieved is that the locking element indeed moves at the point in time when the hinge is swayed with respect to the vertical.

According to the invention it is advantageous that the hinge is provided with a displacement mechanism for forcing the locking element into, respectively, the first or the second position thereof.

In this context it is advantageous that the displacement mechanism comprises a control element that can be operated by hand.

In practice, situations are conceivable where a user will him/herself want to be able to exert influence on whether or not the hinge in a knee joint is unlocked or locked. This is the case, for example, when a user wants to sit down. In this context it is advantageous if the user has, for example, a control element that can be operated by hand in order to move the locking element from the second position, in which the hinge is locked, into the first position of the locking element, in which the locking element releases the hinge.

The opposite case is also conceivable. In this case the user wants, for example, to lock the hinge when the user takes a step backwards. For both of these applications it is advantageous if the user is able, for example, to change the position of a pawl by hand, which pawl is connected to the locking element with the aid of a cable or another mechanism.

According to the invention it is advantageous that the first and the second stop are arranged on a disc, it being possible to rotate or to move the disc with the aid of the displacement mechanism in order to force the locking element into, respectively, the first or the second position thereof.

The disc with the stops thereon is, for example, arranged in the hinge in such a way that the axis of rotation of the disc is coincident with the axis of rotation of the locking element. By this means, by rotating the disc with respect to the axis of rotation the extreme positions of the stops for limiting the locking element in both the first and the second position thereof are changed at the same time. By rotating the disc in a first direction the locking element can be so moved, with the aid of the stops, that it always releases the hinge. By rotating the disc in the opposing direction the locking element is so manipulated by the stops that it locks the hinge at all times.

According to the invention it is furthermore advantageous that the locking element is constructed as a body for transmitting forces from the second part via the locking element to the first part.

As a result of this measure, forces which are exerted on the first part are transmitted via the locking element to the second part. In order to prevent the pivot pin of the locking element being subjected to excessive stress as a result of the transmission of the forces from the first part to the second part, it is advantageous that the locking element is connected to the pivot pin thereof via a flexible element, such as a rubber ring.

According to the invention, it is furthermore advantageous that the locking element is provided with an adjusting body for adjusting the center of gravity of the locking element with respect to the axis of rotation thereof.

It is possible to adjust the hinge with the aid of the adjusting body. The user can him- or herself, according to need, select the point in time at which the locking element swings under the influence of gravity from the first position into the second position thereof.

The invention further relates to an orthesis provided with a first part that is provided with means for attaching the first part to a first part of the body or replacement body part and a second part that is provided with means for attaching the second part to a second part of the body or replacement body part. The particular feature of the orthesis according to the invention is that this is provided with a hinge according to the invention.

As already indicated above, the hinge according to the present invention is in particular suitable for use in an orthopedic knee joint.

BRIEF DESCRIPTION OF THE DRAWINGS

The invention will be further explained with reference to the appended figures, in which.

DETAILED DESCRIPTION OF THE PREFERRED EMBODIMENTS

Figure 1:
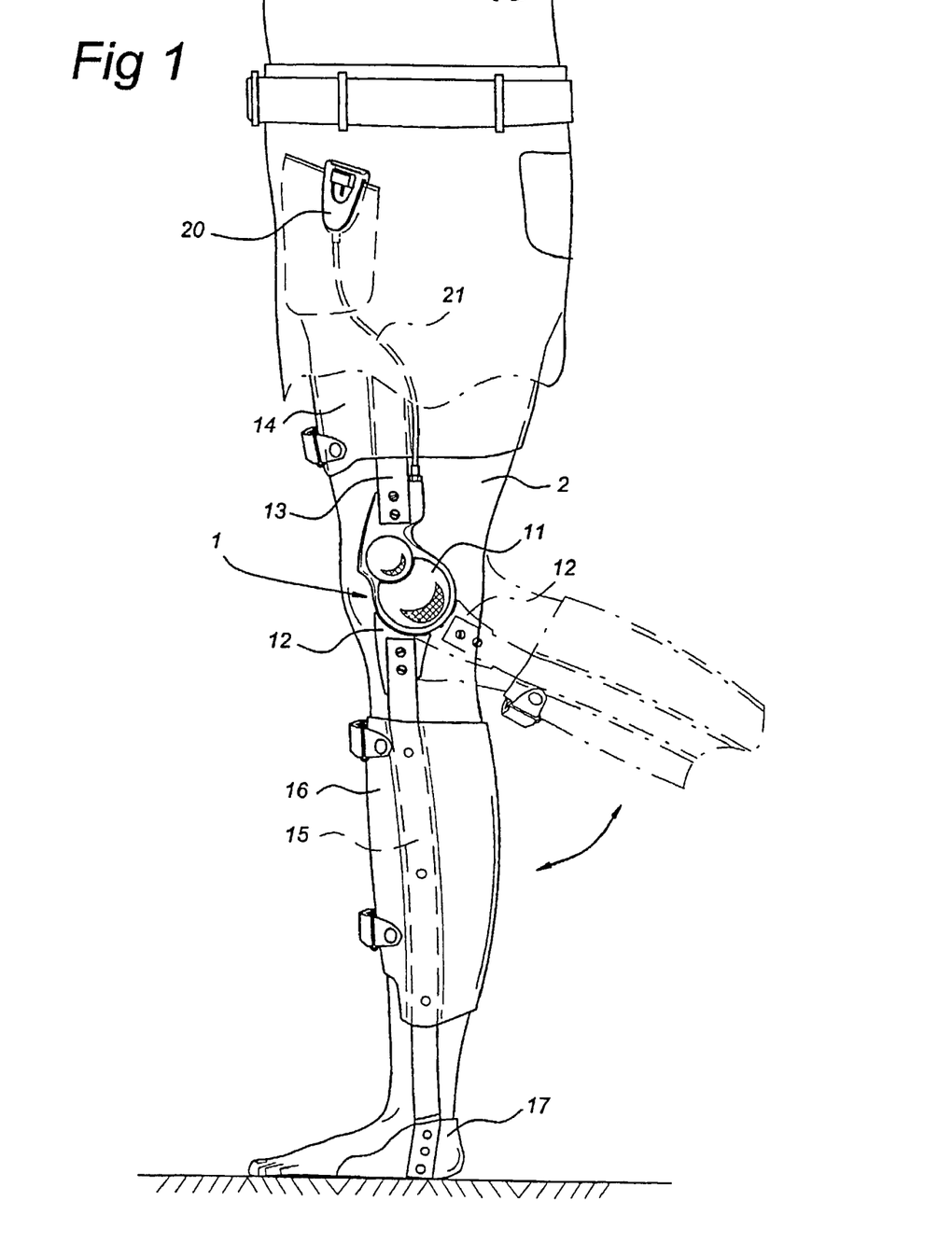
FIG. 1 shows a view of the hinge according to the invention incorporated in an orthopedic leg orthesis.

FIG. 1 shows the hinge 1 that is incorporated in an orthopedic knee joint. The orthopedic knee joint is attached to one leg 2 of a user. The orthopedic knee joint 1 comprises a first part 11 and a second part 12 that are connected to one another such that they can turn. The first part 11 is provided with a bracket 13 on which a fixing element 14 is mounted. Said fixing element 14 is used to attach the orthopedic knee joint to a user's thigh. In the same way, the second part 12 of the hinge 1 is provided with a bracket 15 on which a second fixing element 16 is fixed for attaching the orthopedic knee joint to the user's lower leg. In addition, a support 17, for supporting the user's foot, is fitted at the end of the bracket 15. The hinge 1 can be locked with the aid of a locking element. This is further explained with reference to FIGS. 2 and 3. During the walking movement of a user, this locking element can be moved from a first position for releasing the hinge 1 into a second position for locking the hinge 1. When the hinge 1 is locked, the first part 11 is fixed with respect to the second part 12. That is to say, a user can safely place weight on the leg 2 in the knowledge that the knee is locked. At the point in time when the user has moved his/her body so far that the leg 2 extends somewhat towards the rear with respect to the body, that is to say the end of the stage in which stress is placed on the leg 2, the locking element (see FIGS. 2 and 3) will move into the first position thereof in order to release the hinge 1. That is to say from the point in time when the swinging phase of the leg starts, the second part 12 is able to pivot with respect to the first part 11. This is shown in broken lines in FIG. 1. By making use of the hinge 1 according to the present invention, a user who him- or herself is unable to stabilise his/her knee is able to walk normally as if he/she had a normal leg.

Situations are conceivable in which the user him- or herself wants to be able to influence whether or not the hinge 1 is locked. The hinge 1 according to the present invention is therefore provided with a displacement mechanism such as control element 20 (FIG. 1) that can be operated by hand. With the aid of this element 20, the locking element in the hinge 1 can be deliberately moved into the first position in order to release the hinge or into the second position in order to lock the hinge. In this context consideration can be given, for example, to a point in time when a user wants to sit down. In this case the user will want to unlock the hinge him- or herself. If a user wants to place weight on the leg, for example as he or she takes a step backwards, the user can deliberately lock the knee with the aid of the control element 20. The element 20 is, for example, connected to the first part 11 of the hinge 1 with the aid of a cable 21.

Figure 2:
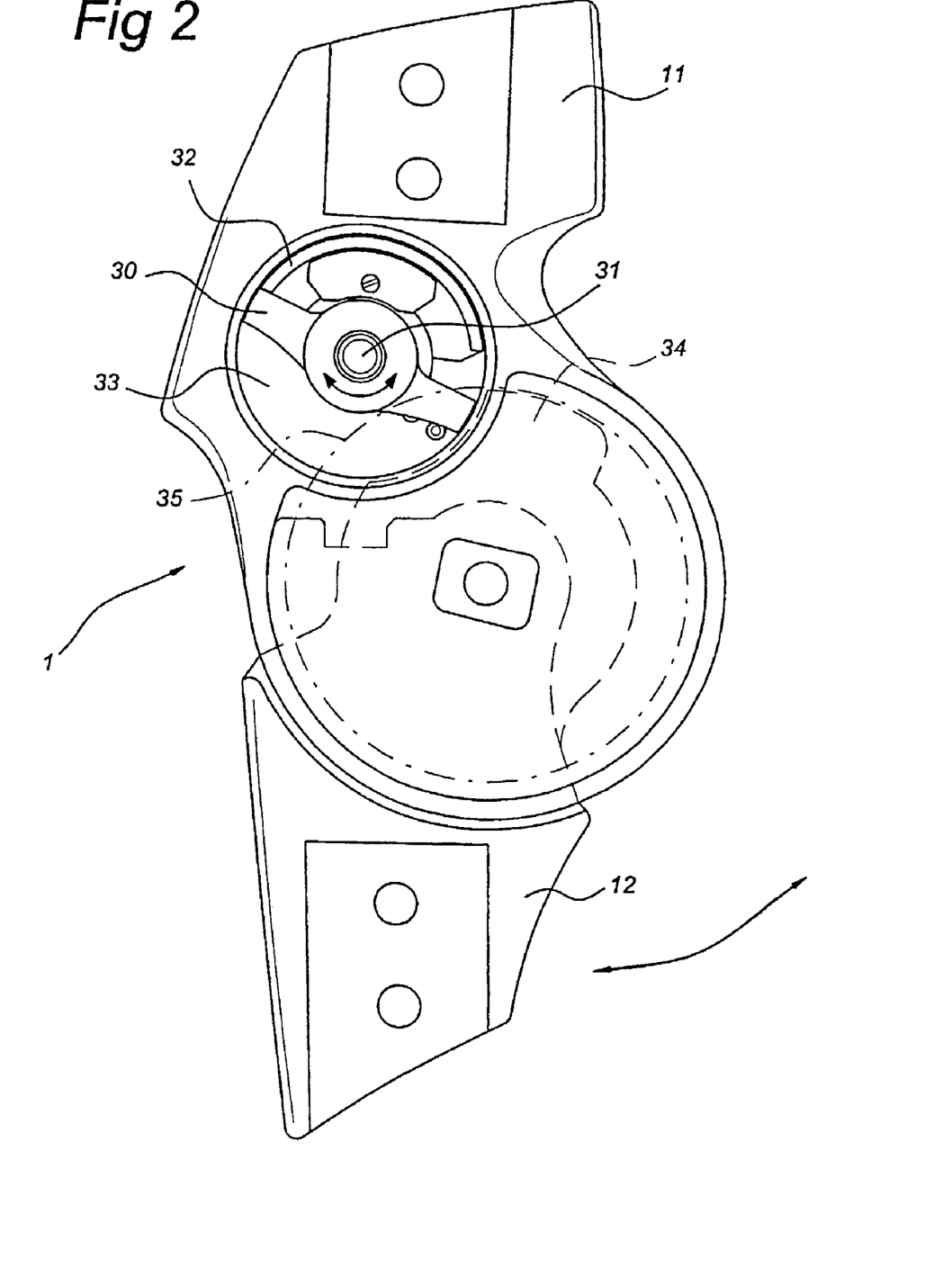
FIG. 2 shows a detail of an exposed view of a hinge according to the invention in the first position thereof, in which the locking element locks the hinge.
Figure 3:
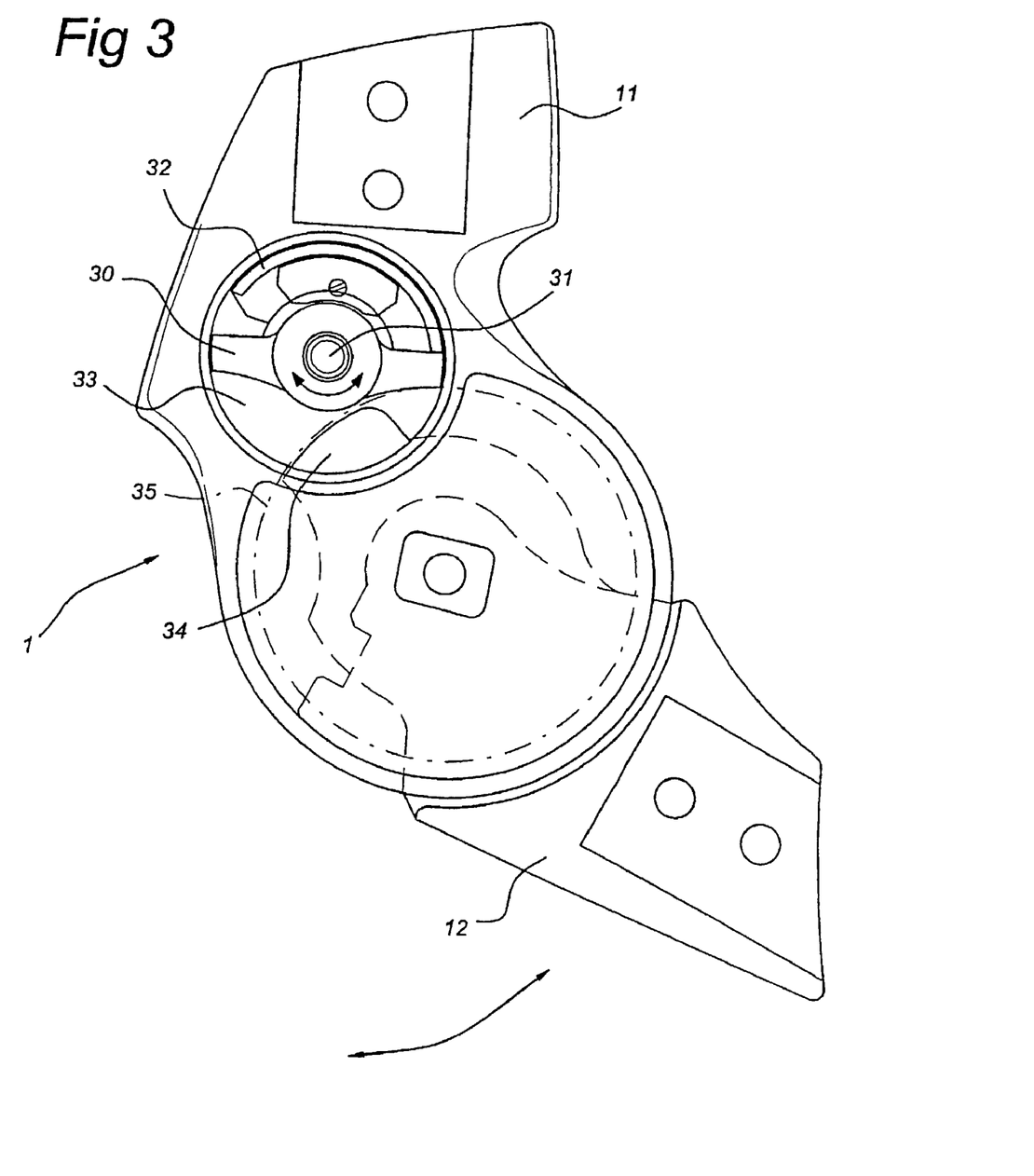
FIG. 3 shows an exposed view of the hinge according to the invention in the second position thereof, in which the locking element releases the hinge.

The hinge 1 according to the present invention is again shown in FIG. 2. In FIG. 2 the hinge 1 is shown in a somewhat exposed view so that the interior of the hinge 1 can be seen. A locking element 30 fitted such that it can pivot. This locking element 30 is fixed to a pivot pin 31 so that it can turn. The locking element 30 is fixed to the pivot pin 31 with the aid of a flexible element, such as, for example, a rubber ring. The turning movement of the locking element 30 is limited by means of a stop 32. This stop 32 is mounted on a disc 33. This disc 33 has the same point of rotation as the locking element 30. The extreme positions of the turning movements of the locking element 30 are determined by the presence of the stop 32. Because the stop 32 is itself fixed to a disc 33, the position of the stop 32 relative to the hinge 1 can be moved. The locking element 30 can be brought into the first or into the second position thereof by rotating the disc 33. According to FIG. 2, the locking element 30 is in the second position. The locking element 30 is then in the path of a projection 34 on the second part 12. This path is shown with the aid of a dotted line 35. When the hinge 1 is swayed in its entirety, the locking element 30 will be able to pivot in the anticlockwise direction under the influence of gravity. As a result the locking element 30 comes into the first position thereof in order to release a hinge. This situation is shown in FIG. 3. The hinge 1 according to the invention is again shown in FIG. 3. According to FIG. 3, the second part 12 has pivoted relative to the first part 11. This is possible because the locking element 30 has now moved out of the path 35 of the projection 34.

Figure 4:
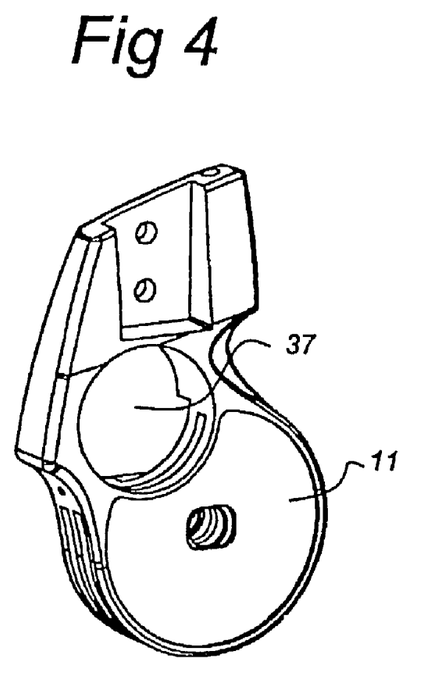
FIG. 4 shows a perspective view of the first part of the hinge according to the invention from a first side.
Figure 5:
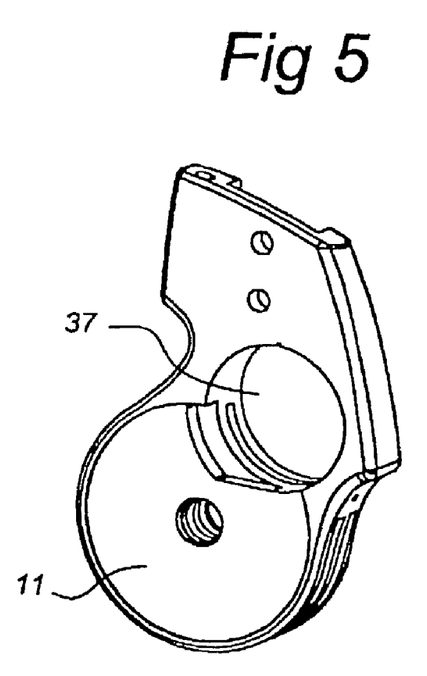
FIG. 5 shows the first part of the hinge according to the invention in a perspective view from the second side.
Figure 6:
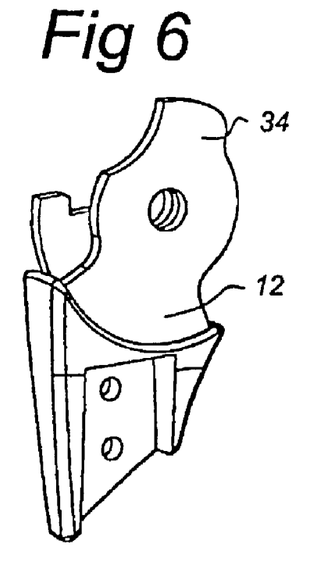
FIG. 6 shows the second part of the hinge according to the invention in a perspective view, seen from a first side.
Figure 7:
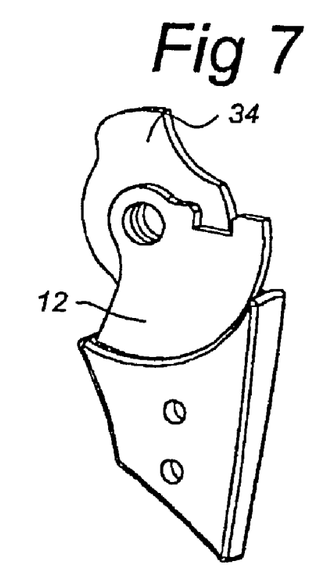
FIG. 7 shows a second view of the second part according to FIG. 6.

A perspective view of a possible embodiment of the first part 11 according to the present invention is shown in FIGS. 4 and 5. A possible embodiment of the second part 12 of the hinge according to the invention is shown in FIGS. 6 and 7. As can be seen if FIGS. 4–7 are taken together, the second part 12 extends at least partially through the body of the first part 11. With this arrangement the projection 34 on the second part 12 extends into the opening 37 that has been made in the body of the first part 11.

Figures 8, 9, 10:
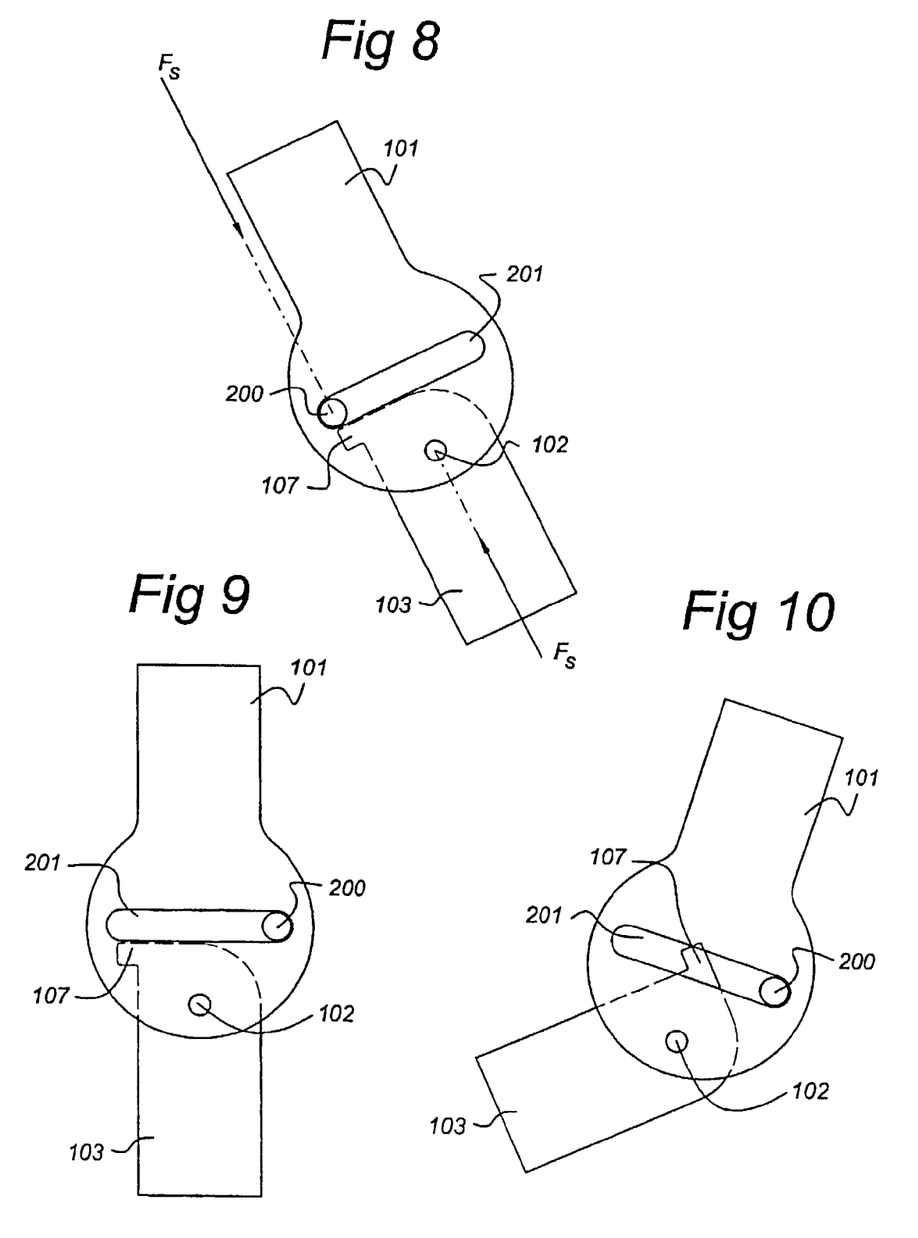
In FIGS. 8, 9 and 10 the operating principle of a knee joint according to the invention is shown diagrammatically, a rotatable coupling element being fitted in the hinge within a guide.

The principle of a knee joint is shown diagrammatically in FIGS. 8, 9 and 10, which joint comprises a upper part 101 that can be attached to a user's thigh via an extension piece, which is not shown, or via a pin. The upper part 101 is connected via hinge 102 to a lower part 103 that can be connected via an extension piece, which is not shown, to a user's lower leg or lower leg prosthesis. As has already been stated above, in order to obtain a walking movement that is as natural as possible the upper part must be locked with respect to the lower part during that part of the walking movement in which the leg is pointing forwards; see FIG. 8. This locking must be maintained until approximately the mid-position, see FIG. 9, and thereafter the two parts must be unlocked during the backward swing, so that the lower leg is able to swing backwards, see FIG. 10. In this embodiment this is achieved by a blocking mechanism which comprises a cylinder or ball 200 that is able to execute a rolling or sliding back-and-forth movement between two stable positions in guide 201. In the position in FIG. 8, a torque Fs—Fs is acting in the joint, the one force of which passes through the hinge 102 and the other force of which passes through the cylinder/ball 200 and projection 107, as a result of which the two parts are locked with respect to one another. When the leg is swung backwards, just beyond the mid-position, in FIG. 9, gravity forces the cylinder/ball into its other stable position, as a result of which the upper and lower parts are unlocked so that, as shown in FIG. 10, the lower leg part is able to pivot relative to the thigh part. The leg can now be bent. In this way a knee joint is obtained that makes a virtually natural walking movement possible.

Figure 31:
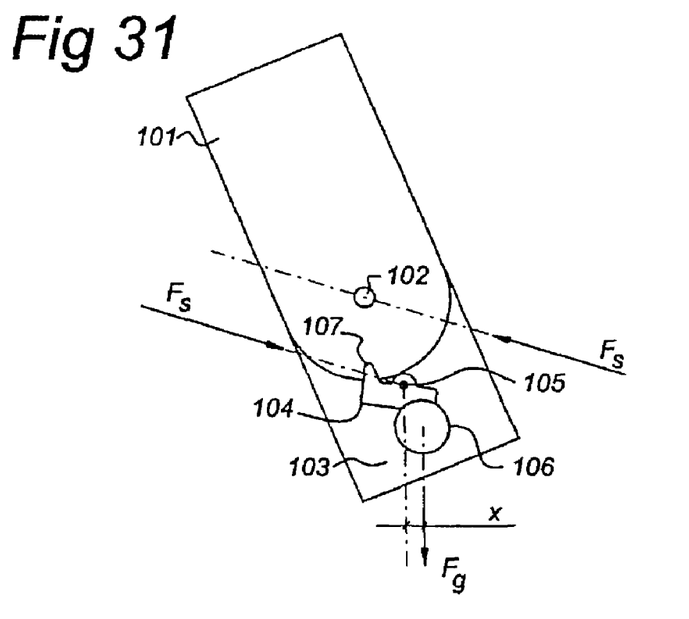
FIGS. 31–33 show a further variant.
Figure 32:
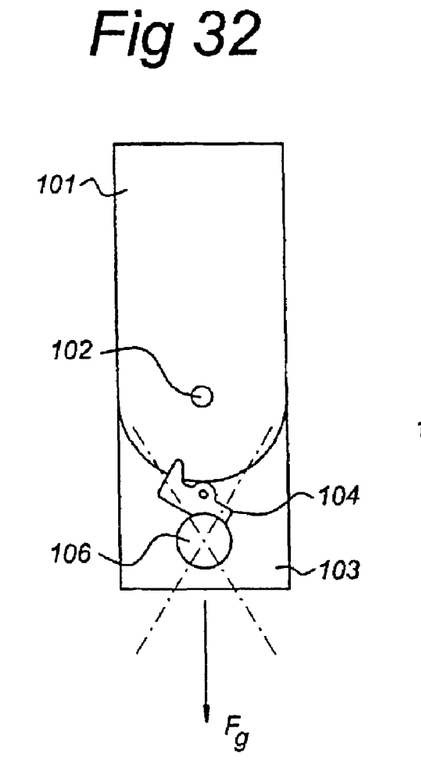
Figure 33:
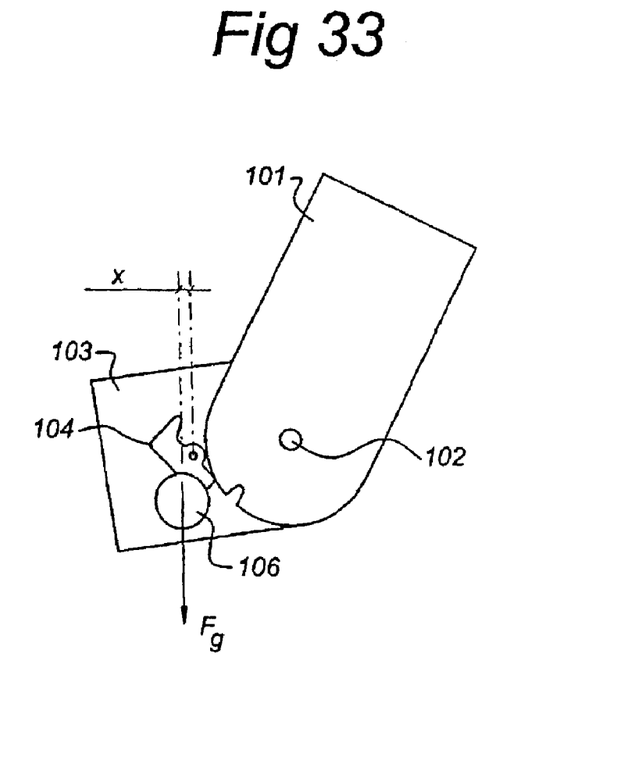

A variant of this embodiment is shown in FIGS. 31–33, with a blocking mechanism which comprises a pawl 104 that can be pivoted about a pin 105 and on one side of pin 105 is coupled to a weight 106. On the other side pawl 104 is provided with a projection 107 that is able to engage in a recess in the upper part. In the position in FIG. 31, a torque Fs—Fs acts on the leg, the one force of which passes through hinge 102 and the other force of which passes through projection 107. Gravity Fg acts on the weight 106 along a line that is located a distance x to the right of the pin 105 of the pawl 104, so that a torque acting to the right is exerted on this pawl, which torque forces the projection 107 into the recess and thus locks upper and lower part with respect to one another. When the leg is swung backwards, the distance x becomes zero in the mid-position, FIG. 32, and, when the leg is swung further backwards, x is to the left of the pin 105, as a result of which a torque acting to the left is then exerted on pawl 104, as a result of which the pawl pivots to the left and the projection 107 disengages from the recess and upper and lower part are unlocked.

Figure 11:
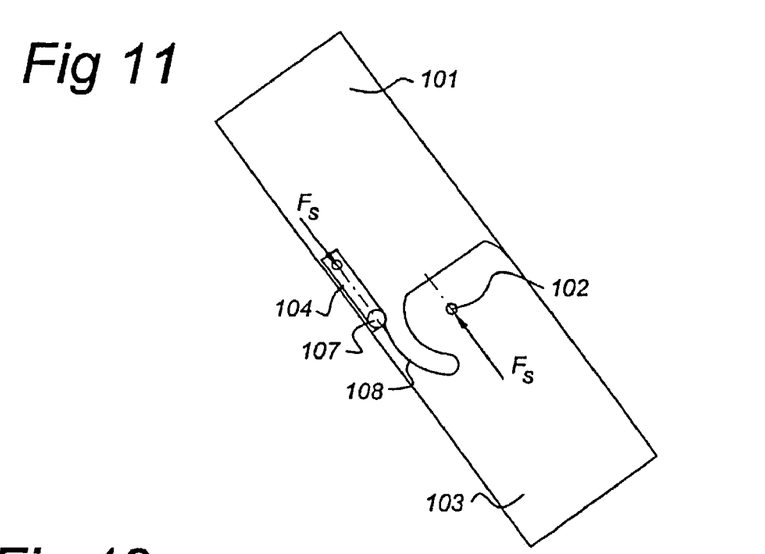
FIGS. 11, 12 and 13 show, diagrammatically, the principle of a corresponding knee joint, where the locking element is now provided with a pawl that can be accommodated in a guide slot.
Figure 12:
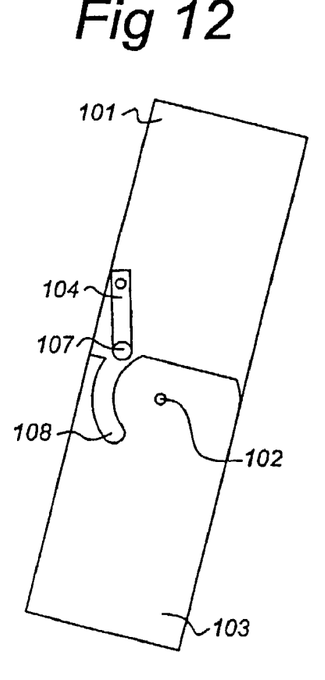
Figure 13:
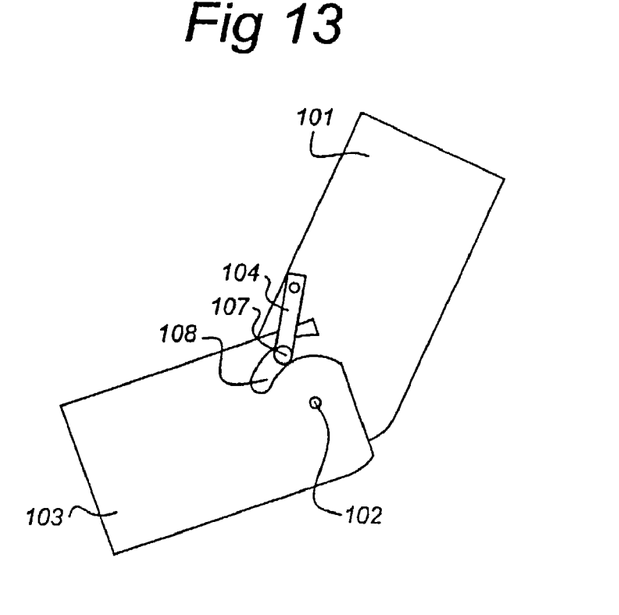

One problem that can arise with this embodiment is that the pawl 104, with pendulum weight 106 attached thereto, starts to oscillate freely at its natural frequency. The question then is whether the pawl will return to the correct position at the correct point in time. In order to overcome this problem, in the embodiment according to FIGS. 11, 12 and 13 the pawl 104, which is now pivotably attached to the upper part, is provided with a projection 107 that in one position, FIG. 11, bears on a surface of the lower part to produce locking and in the unlocked position is accommodated in a slot 108 in the lower part and is guided in said slot. In this way the movement of the pawl 104 is controlled in both positions.

Figure 14:
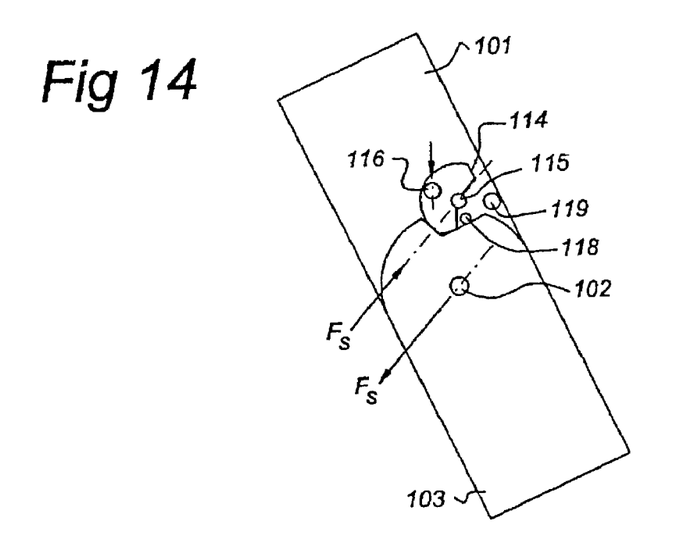
FIGS. 14, 15 and 16 show, diagrammatically, a knee joint with a pivotable locking element, the center of gravity of which is located above the pivot pin.
Figure 15:
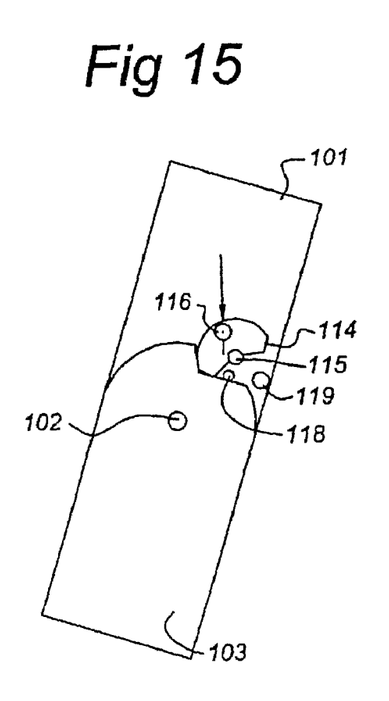
Figure 16:
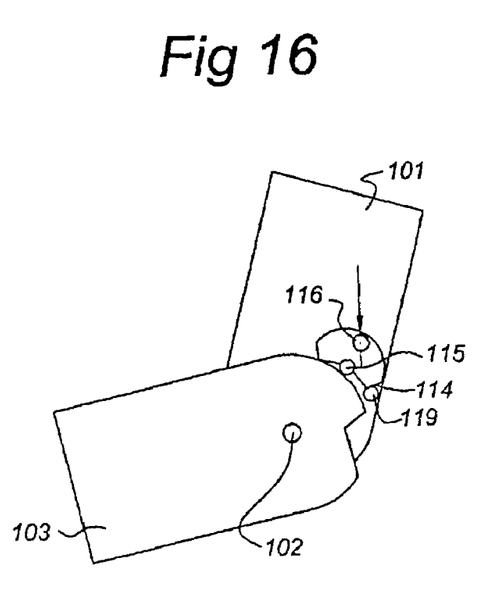

Another embodiment of the joint is shown in FIGS. 14, 15 and 16, a bi-stable element 114, which has a center of gravity 116 located above the pivot pin 115 thereof, now being used as locking element. When the leg is in the position according to FIG. 14, where the leg is pointing forwards, the center of gravity 116 is to the left of the pin 115, so that the element has flipped over to the left and is in contact with a first stop 118 and in that position locks upper and lower part to one another. When the leg is in the position according to FIG. 15, the center of gravity 116 is virtually above the pin 115, but still to the left thereof, so that the joint is still locked. As the leg continues to swing, the center of gravity 116 will move to the right of the pivot pin 115 and as a consequence the element 114 will flip over into its second position in FIG. 16, the element then bearing on a second stop 119 and the two parts of the joint being unlocked. Free oscillation of the element 114 will not be possible with this embodiment.

A further embodiment of the principle described above is also shown in FIGS. 17 and 18, identical components being indicated by the same reference numerals in these figures. The construction and mode of operation of this embodiment will be clear following the above. It is also pointed out that the tilting moment of element 114 can be influenced by, for example, making a hole 216 in one side of the element.

Figure 19:
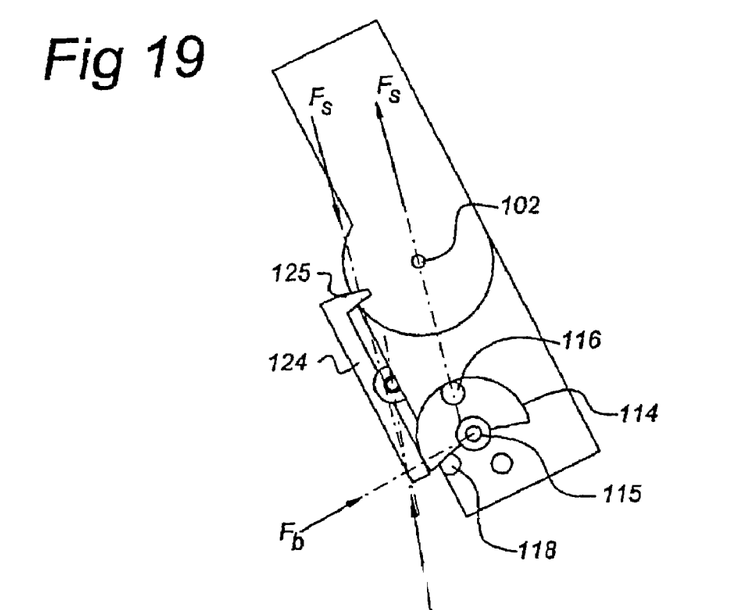
FIGS. 19, 20 and 21 show a joint as in FIGS. 14, 15 and 16, where use is made of a lever, for enhancing the power, between the pivotable locking element and a blocking projection.
Figure 20:
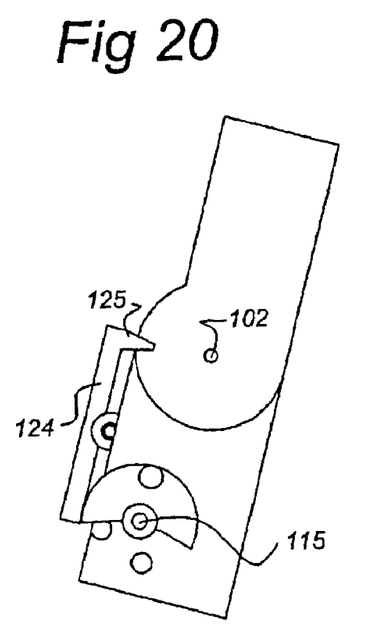
Figure 21:
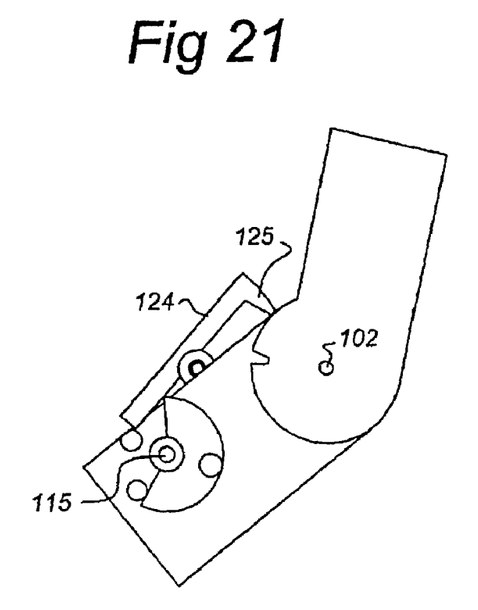

FIGS. 19, 20 and 21 show, diagrammatically, an embodiment of the joint in which the locking element 114 again has a center of gravity 116 that is located above the pivot pin and thus will assume two positions depending on the position of the leg. In this case the element 114 cooperates with a lever 124, so that the power of element 114 is enhanced and the projection 125 at the end of the lever 124 will be forcefully pushed into the recess in the other joint part.

Figure 17:
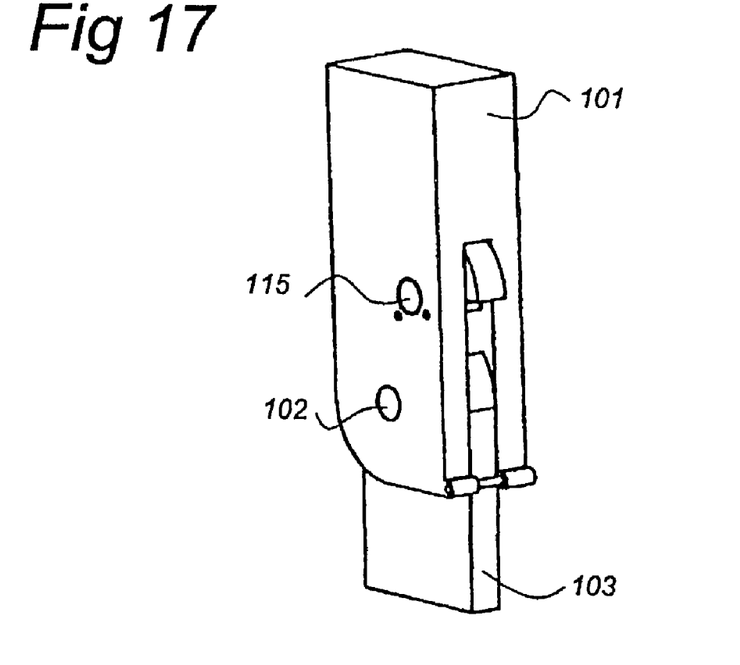
FIGS. 17 and 18 show, diagrammatically, a further development of the joint according to FIGS. 14, 15 and 16.
Figure 18:
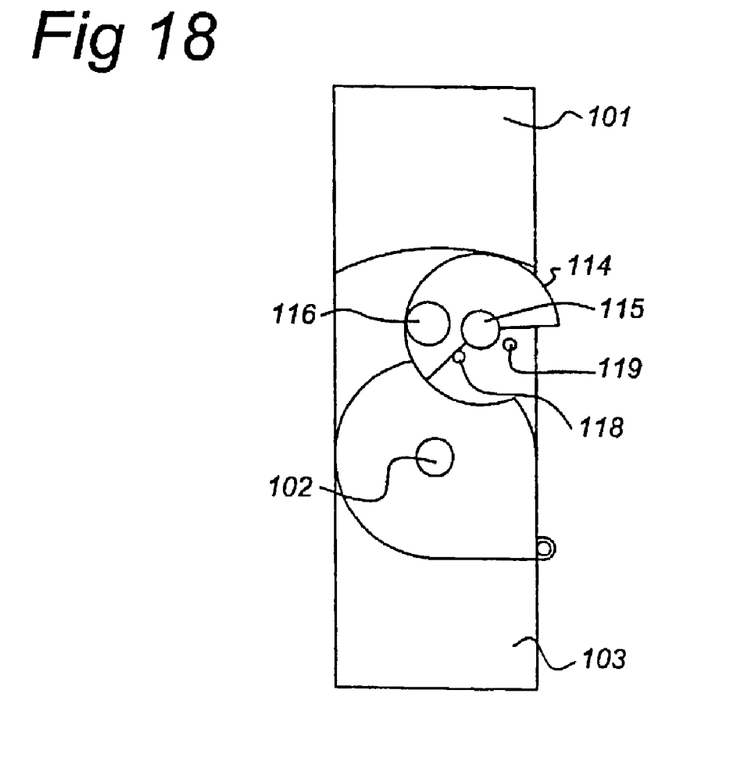
Figure 22:
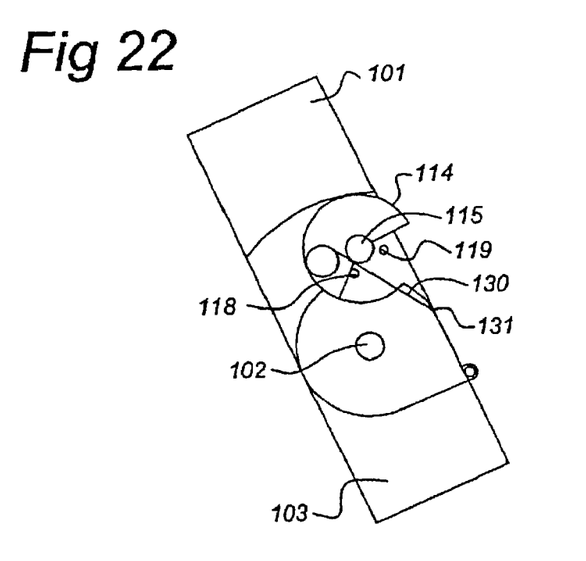
FIGS. 22, 23 and 24 and FIGS. 25, 26 and 27 show knee joints in which the position of the blocking mechanism is assisted by means of spring tension.
Figure 23:
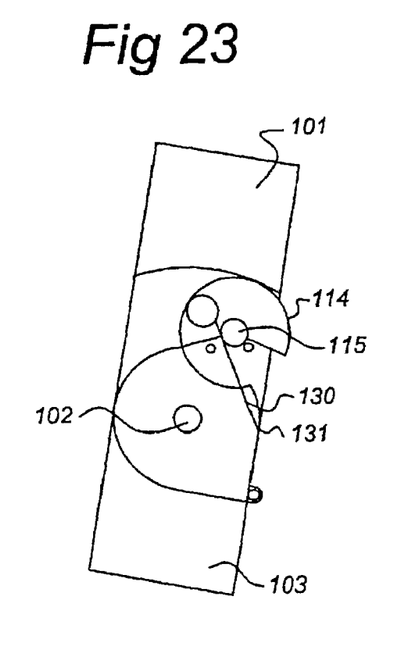
Figure 24:
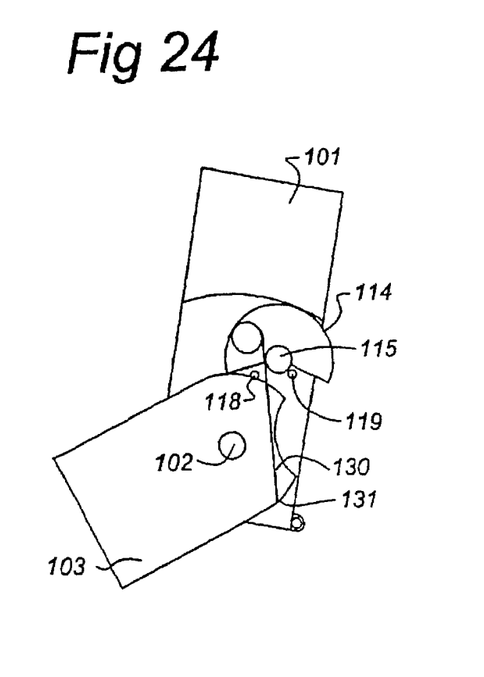

FIGS. 22, 23 and 24 show the same embodiment of the joint as in FIGS. 17, 18, except that the locking element 114 is now coupled via an extension spring 130 to a point 131 on the lower part 103 and specifically is coupled in such a way that in the situation in FIG. 22 the locking element 114 is in contact with stop 118, the two joint parts are locked and the extension spring 130 is not under strain. With this arrangement, the element 114 is trapped between the two joint parts and shocks will have no influence on its position. In the situation in FIG. 24, the two joint parts are unlocked and the extension spring 130 is stretched by bending of the lower leg, so that the element 114 is pulled towards the curved surface of the lower part. Any shocks to the leg will now not result in the element 114 switching to a different position.

Figure 25:
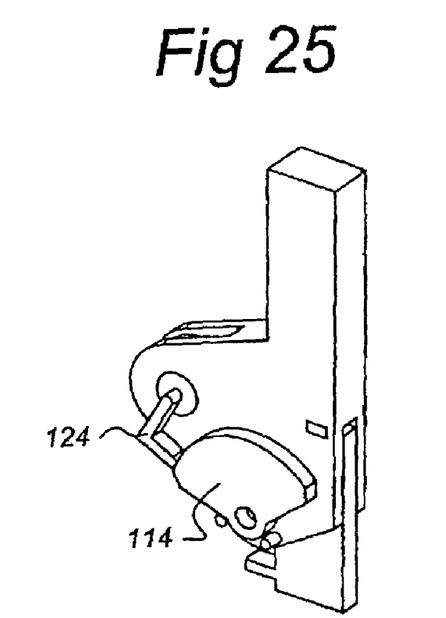
Figure 26:
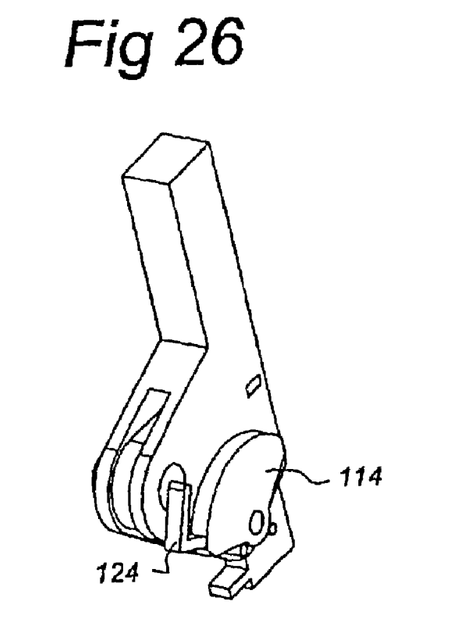
Figure 27:
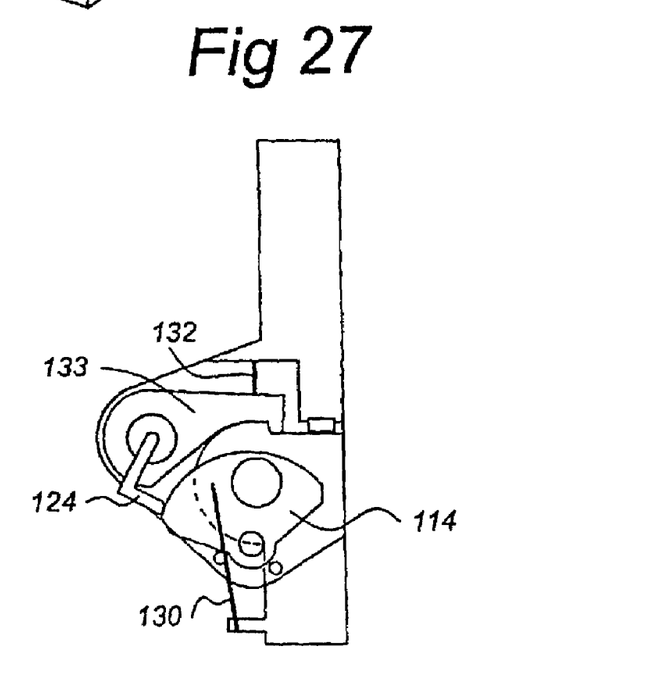

FIGS. 25, 26, 27 also show an embodiment which has extension springs 130 and 132 in order to ensure that shocks to the leg do not result in any undesired change in position of the element 114. One difference compared with the embodiment according to the preceding figure is that the element 114 now interacts with a lever 124 that is connected to a pawl 133 which provides the final locking.

Figure 28:
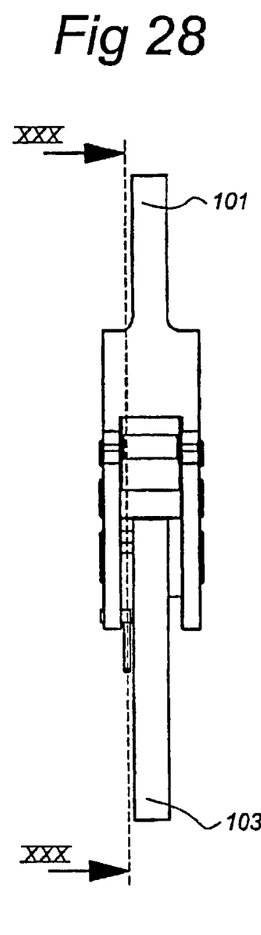
FIGS. 28, 29 and 30 show an embodiment of a knee joint in two mutually perpendicular views and in a cross-section along the line XXX—XXX in FIG. 28.
Figure 29:
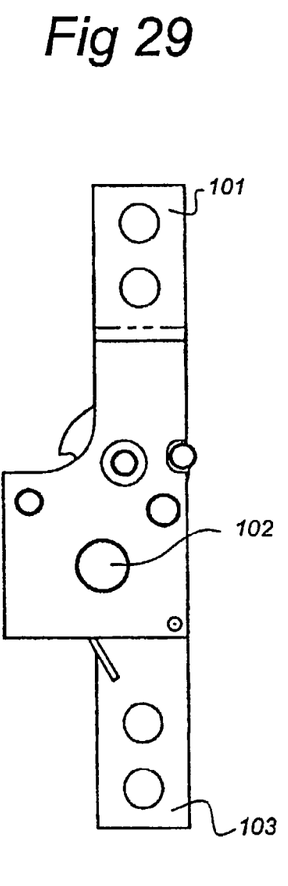
Figure 30:
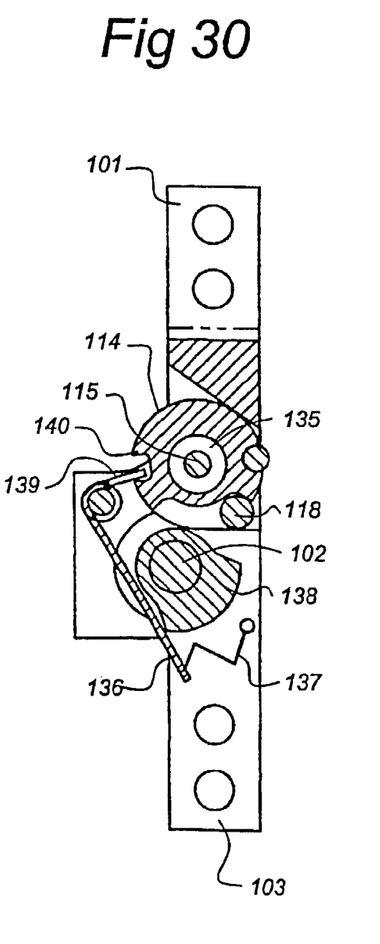

FIGS. 28, 29, 30 show an embodiment in two mutually perpendicular views and a cross-section along the line XXX—XXX. In this embodiment the two joint parts 101 and 103 are again connected by hinge 102. A locking element 114 is once again mounted in a bearing, using a ball bearing 135, on the upper part 101 such that it can pivot. The location of the center of gravity above the pivot pin 115 again ensures that the element 114 is again able to assume two positions, in which it is then in contact with the stop 118 depending on the position of the leg. With this arrangement, in the one position the joint is again locked whilst in the other position the joint is unlocked. In order to ensure that the element in the unlocked situation will not execute any undesired movement under the influence of shocks, with this embodiment as well a spring 136 is fitted that at one end is pulled by an auxiliary spring 137 into contact with a projection 138 on the lower part 103 and at the other end engages by a part 139 into a recess 140 in the locking element 114. In this way the effect of shocks on the position of the locking element is effectively and simply eliminated.

In order to prevent the pin 115 from being damaged when the joint is in the locked position, as a result of the forces exerted thereon by the lower part, the ball bearing 135 is accommodated via an elastic layer, which is not shown, preferably in the form of an O-ring, in the bore in the upper part. If forces are now exerted by the lower part 103 on the element 114, the bearing 115 will, as a consequence of the elastic layer, move to some extent in its bore until the other side of the element is in contact with the surface of the upper part and the forces are absorbed by this.

What is claimed is:

1. An orthopedic hinge, comprising:
a first part provided with means for attaching the hinge to a first body part or replacement body part;
a second part provided with means for attaching the hinge to a second body part or replacement body part, the first part and the second part being able to turn with respect to each other between a first position wherein the second part is essentially an extension of the first part, and a second position wherein the second part is at an angle with respect to the first part; and
a locking element that is movable between a locking position and a release position, the locking element locks the first part and the second part with respect to each other in the locking position, the locking element enables relative movement of the first and the second part with respect to each other in the release position,
wherein the lock element is fixed in the hinge in such a way that the locking element is able to turn, the locking element being able to pivot about the axis of rotation of the locking element under the influence of gravity from the locking position to the release position.

2. The hinge according to claim 1, wherein the center of gravity of the locking element is spaced apart from the axis of rotation of the locking element.

3. The hinge according to claim 1, wherein the center of gravity of the locking element is located above the axis of rotation of the locking element when the hinge is being used.

4. An orthopedic hinge, comprising:
a first part provided with means for attaching the hinge to a first body part or replacement body part;
a second part provided with means for attaching the hinge to a second body part or replacement body part, the first part and the second part being able to turn with respect to each other between a first position wherein the second part is essentially an extension of the first part, and a second position wherein the second part is at an angle with respect to the first part; and
a locking element that is movable between a locking position and a release position, the locking element locks the first part and the second part with respect to each other in the locking position, the locking element enables relative movement of the first and the second part with respect to each other in the release position, wherein the locking element is pivotable about a pivot axis between the locking position and the release position, and the center of gravity of the pivotable locking element is spaced apart from the pivot axis, so that the locking element is movable due to the influence of gravity.

5. The hinge according to claim 4, wherein the second part is provided with a projection, said projection describes a path when the second part pivots relative to the first part, the locking element allowing the projection a free movement path when the locking element is in the release position and being present in the movement path of the projection when the locking element is in the locking position.

6. The hinge according to claim 4, wherein the hinge is provided with a first and a second stop in order to limit the movement of the locking element in, respectively, the release and the locking position.

7. The hinge according to claim 6, wherein the hinge is provided with a displacement mechanism for forcing the locking element into, respectively, the release or the locking position.

8. The hinge according to claim 7, wherein the displacement mechanism comprises a control element that can be operated by hand.

9. The hinge according to claim 7, wherein the first and the second stop are arranged on a disc, it being possible to rotate the disc with the aid of the displacement mechanism in order to force the locking element into, respectively, the release or the locking position.

10. The hinge according to claim 7, wherein the locking element is fixed in the hinge in such a way that it is able to slide, the locking element being able to move about the axis of rotation of the locking element under the influence of gravity.

11. The hinge according to claim 10, wherein the first and second stop are arranged on a disc, it being possible to move the disc with the aid of the displacement mechanism in order to force the locking element into, respectively, the release or the locking position thereof.

12. The hinge according to claim 4, wherein the locking element is constructed as a body for transmitting forces from the second part via the locking element to the first part.

13. The hinge according to claim 12, wherein the locking element is connected to a pivot pin of the locking element via a flexible element.

14. The hinge according to claim 4, wherein the locking element is provided with an adjusting body for adjusting the center of gravity of the locking element with respect to the axis of rotation of the locking element.

15. An orthopedic orthesis or prothesis wherein the orthesis or prothesis is provided with a hinge according to claim 4.

16. The orthopedic hinge according to claim 4, wherein the locking element is movable under the influence of gravity from the locking position to the release position upon swaying the hinge in the first position of the first part and the second part from an essentially vertical plane in a direction corresponding to a leg swung in a backward direction.

17. The orthopedic hinge according to claim 4, wherein the locking element is movable under the influence of gravity from the release position to the locking position upon swaying the hinge in the first position of the first part and the second part from an essentially vertical plane in a direction corresponding to a leg swung in a forward direction.

18. The orthopedic hinge according to claim 4, wherein the center of gravity of the pivotable locking element in the locking position is on a first side of a vertical plane through the pivot axis, and wherein the center of gravity of the pivotable locking element in the release position is on a second side of said vertical plane, said second side is opposed to said first side.

19. The orthopedic hinge according to claim 4, wherein during use, the center of gravity of the pivotable locking element is located above the pivot axis.

20. The orthopedic hinge according to claim 4, wherein the locking element comprises a bi-stable element.

21. The orthopedic hinge according to claim 4, wherein during use, the center of gravity of the pivotable locking element is located below the pivot axis.

22. The orthopedic hinge according to claim 4, wherein the locking element comprises a pendulum weight that is located below the pivot axis during use.

23. An orthopedic hinge, comprising:

a first part connectable to a first body part;

a second part connectable to a second body part different from said first body part, said first and second parts being able to turn relative to one another from a first hinge position to a second hinge position; and a locking element for locking the hinge in the first hinge position, said locking element being movable between a release position for releasing the hinge and a locking position for locking the hinge, said locking element being movable from the release position to the locking position and from the locking position to the release position due to an influence of gravity, wherein the locking element is pivotable about a pivot axis between the locking position and the release position, and the center of gravity of the pivotable locking element is spaced apart from the pivot axis.

* * * * *